(12) United States Patent
Azernikov et al.

(10) Patent No.: US 11,007,040 B2
(45) Date of Patent: May 18, 2021

(54) DENTAL CAD AUTOMATION USING DEEP LEARNING

(71) Applicant: James R. Glidewell Dental Ceramics, Inc., Newport Beach, CA (US)

(72) Inventors: Sergei Azernikov, Irvine, CA (US); Sergey Nikolskiy, Irvine, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 188 days.

(21) Appl. No.: 15/925,078

(22) Filed: Mar. 19, 2018

(65) Prior Publication Data

US 2019/0282344 A1 Sep. 19, 2019

(51) Int. Cl.
| | |
|---|---|
| A61C 13/00 | (2006.01) |
| A61C 9/00 | (2006.01) |
| G06N 3/08 | (2006.01) |
| G06N 3/04 | (2006.01) |
| G06F 30/00 | (2020.01) |

(52) U.S. Cl.
CPC ........ *A61C 13/0004* (2013.01); *A61C 9/0053* (2013.01); *G06F 30/00* (2020.01); *G06N 3/0454* (2013.01); *G06N 3/08* (2013.01)

(58) Field of Classification Search
CPC ... A61C 13/0004; A61C 9/0053; G06F 30/00; G06N 3/0454; G06N 3/08
USPC .......................................................... 433/213
See application file for complete search history.

(56) References Cited

U.S. PATENT DOCUMENTS

| | | | |
|---|---|---|---|
| 6,409,504 B1 | 6/2002 | Jones et al. | |
| 7,084,868 B2 | 8/2006 | Farag et al. | |
| 7,702,492 B2 | 4/2010 | Marshall | |
| 7,708,557 B2 | 5/2010 | Rubbert | |
| 8,126,726 B2 | 2/2012 | Matov et al. | |
| 8,454,362 B2 | 6/2013 | Rubbert | |
| 8,602,780 B2 | 12/2013 | Rubbert | |
| 9,417,700 B2 | 8/2016 | El Dokor et al. | |
| 9,474,582 B2 | 10/2016 | Musuvathy et al. | |
| 2002/0015934 A1 | 2/2002 | Rubbert et al. | |
| 2005/0192835 A1 | 9/2005 | Kou et al. | |
| 2007/0183633 A1 | 8/2007 | Hoffman | |
| 2013/0244208 A1 | 9/2013 | Rubbert | |
| 2017/0045950 A1 | 2/2017 | El Dokor et al. | |
| 2017/0340418 A1 | 11/2017 | Raanan | |

(Continued)

FOREIGN PATENT DOCUMENTS

| | | |
|---|---|---|
| DE | 102017203475 A1 | 9/2018 |
| WO | 2018158411 A1 | 9/2018 |

OTHER PUBLICATIONS

Stefan Raith, et al., Artificial Neural Networks as a powerful numerical tool to classify specific features of a tooth based on 3D scan data. Elsevier, Computers in Biology and Medicine 80 (2017), pp. 65-76.

*Primary Examiner* — Matthew M Nelson

(74) *Attorney, Agent, or Firm* — Charles Fowler; Abhay Kulkarni

(57) ABSTRACT

Computer-implemented methods for generating a 3D dental prosthesis model are disclosed herein. The methods comprise training a deep neural network to generate a first 3D dental prosthesis model using a training data set; receiving a patient scan data representing at least a portion of a patient's dentition; and generating, using the trained deep neural network, the first 3D dental prosthesis model based on the received patient scan data.

22 Claims, 11 Drawing Sheets

(56) References Cited

U.S. PATENT DOCUMENTS

2018/0008213 A1* 1/2018 Rubbert .................. A61K 6/818
2018/0028294 A1* 2/2018 Azernikov ......... A61C 13/0004
2018/0303581 A1 10/2018 Martz
2019/0282344 A1* 9/2019 Azernikov ............... G06N 3/08
2020/0000562 A1* 1/2020 Wey ..................... A61C 9/0046

* cited by examiner

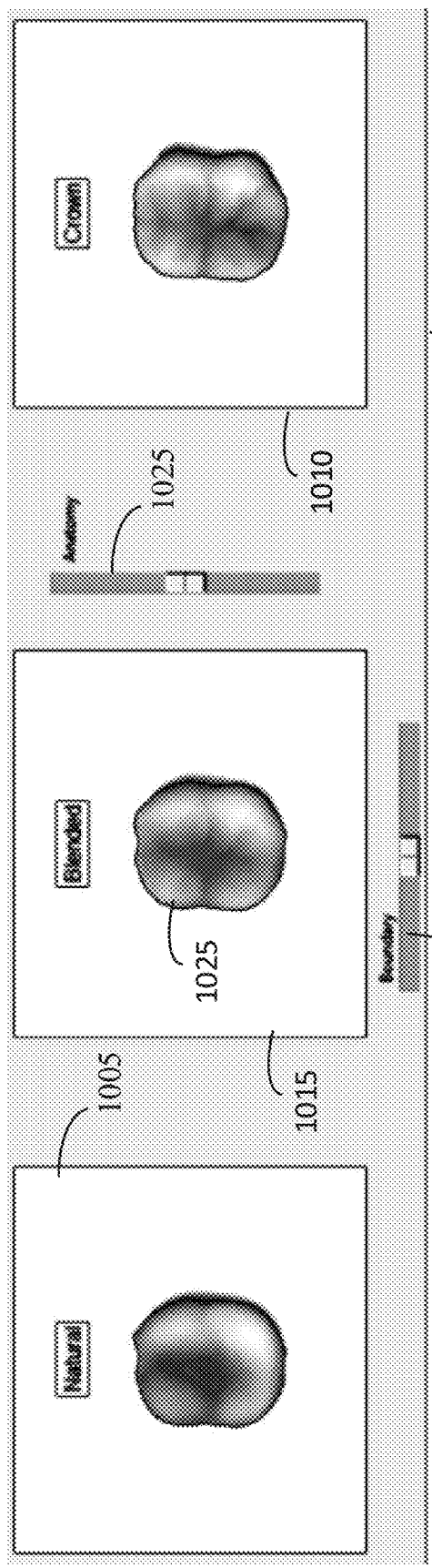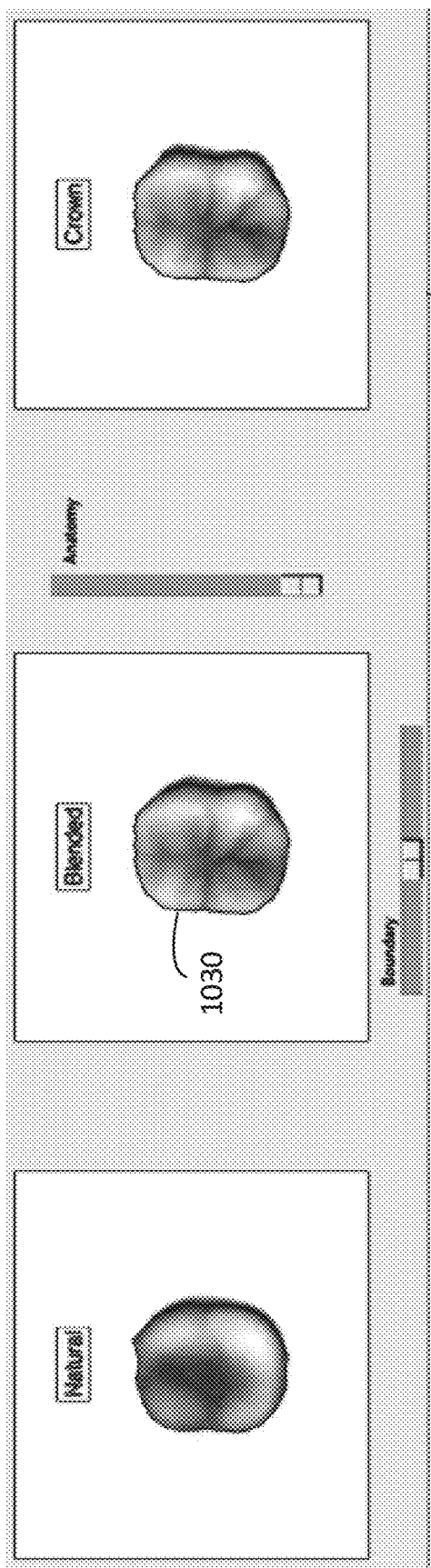
FIG. 10A
FIG. 10B

DENTAL CAD AUTOMATION USING DEEP LEARNING

TECHNICAL FIELD

The disclosure relates generally to the field of dental computer-aided design (CAD), and specifically to dental CAD automation using deep learning.

BACKGROUND

Recently, CAD/CAM dentistry (Computer-Aided Design and Computer-Aided Manufacturing in dentistry) has provided a broad range of dental restorations, including crowns, veneers, inlays and onlays, fixed bridges, dental implant restorations, and orthodontic appliances. In a typical CAD/CAM based dental procedure, a treating dentist can prepare the tooth being restored either as a crown, inlay, onlay or veneer. The prepared tooth and its surroundings are then scanned by a three dimensional (3D) imaging camera and uploaded to a computer for design. Alternatively, a dentist can obtain an impression of the tooth to be restored and the impression may be scanned directly, or formed into a model to be scanned, and uploaded to a computer for design.

Current dental CAD still relies heavily on manual labor. Minimizing the amount of manual labor involved in CAD of those restorations is of high interest. The ultimate goal is to provide a fully-automatic solution which is capable to deliver acceptable designs without human interference. In order to build such a highly autonomous dental CAD system, high level expertise needs to be integrated into the software. One way to do that is to build a comprehensive set of rules that would include all the nuances known to the experienced dental professionals and formulating it in a way machine can understand. However, each dental restoration is unique and certain decisions that are made by dental technicians are very hard to define rigorously. Therefore this is a very tedious task, and obviously feasible only when this set of rules can be provided.

A different approach which has recently gained popularity in the Machine Learning (ML) community is based on an idea to build a system which is capable of learning from a large number of examples without explicit formulation of the rules. This method is commonly referred to as Deep Learning (DL), which is used with certain amount of success in speech recognition (e.g., Siri), computer vision (e.g., Google+), automatic offering (e.g., Amazon) to name a few. Availability of large amounts of data and computational power provide the ability to address problems that seemed intractable just a couple years ago. DL provides the ability to train very large Deep Neural Networks (DNNs) using massive amounts of data.

SUMMARY

Example embodiments of methods and computer-implemented systems for generating a 3D model of a dental prosthesis using deep neural networks are described herein. Certain embodiments of the methods can include: training, by one or more computing devices, a deep neural network to generate a first 3D dental prosthesis model using a training data set; receiving, by the one or more computing devices, a patient scan data representing at least a portion of a patient's dentition; and generating, using the trained deep neural network, the first 3D dental prosthesis model based on the received patient scan data.

The training data set can include a dentition scan data set with preparation site data and a dental prosthesis data set. A preparation site on the gum line can be defined by a preparation margin or margin line on the gum. The dental prosthesis data set can include scanned prosthesis data associated with each preparation site in the dentition scan data set.

The scanned prosthesis can be scans of real patients' crowns created based on a library tooth template, which can have 32 or more tooth templates. The dentition scan data set with preparation site data can include scanned data of real preparation sites from patients' scanned dentition.

In some embodiments, the training data set can include a natural dentition scan data set with digitally fabricated preparation site data and a natural dental prosthesis data set, which can include segmented tooth data associated with each digitally fabricated preparation site in the dentition scan data set. The natural dentition scan data set can have two main components. The first component is a data set that includes scanned dentition data of patients' natural teeth. Data in the first component includes all of the patients' teeth in its natural and unmodified digital state. The second component of the natural dentition scan data is a missing-tooth data set with one or more teeth removed from the scanned data. In place of the missing-tooth, a DNN fabricated preparation site can be placed at the site of the removed tooth. This process generates two sets of dentition data: a full and unmodified dentition scan data of patients' natural teeth; and a missing-tooth data set (natural dental prosthesis data set) in which one or more teeth are digitally removed from the dentition scan data.

In some embodiments, the method further includes generating a full arch digital model and segmenting each tooth in the full arch to generate natural crown data for use as training data. The method can also include: training a second deep neural network to generate a second 3D dental prosthesis model using a natural dentition scan data set with digitally fabricated preparation site data and a natural dental prosthesis data set; generating, using the second deep neural network, the second 3D dental prosthesis model based on the received patient scan data; and blending together features of the first and second 3D dental prosthesis models to generated a blended 3D dental prosthesis model.

In some embodiments, natural dentition scan data can be selected to similarly match the patient's profile such as gender, age, ethnicity, diet, lifestyle, etc. Once the patient's profile is determined, natural dentition scan data having similar or identical profile can be selected to train deep neural networks to generate a customized 3D dental prosthesis.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the disclosed subject matter.

BRIEF DESCRIPTION OF THE DRAWINGS

FIG. 10A-10B illustrates a graphic user interfaces used to transfer/combine features from one dental prosthesis design to another in accordance with some embodiments of the present disclosure.

DETAILED DESCRIPTION

Figure 1:
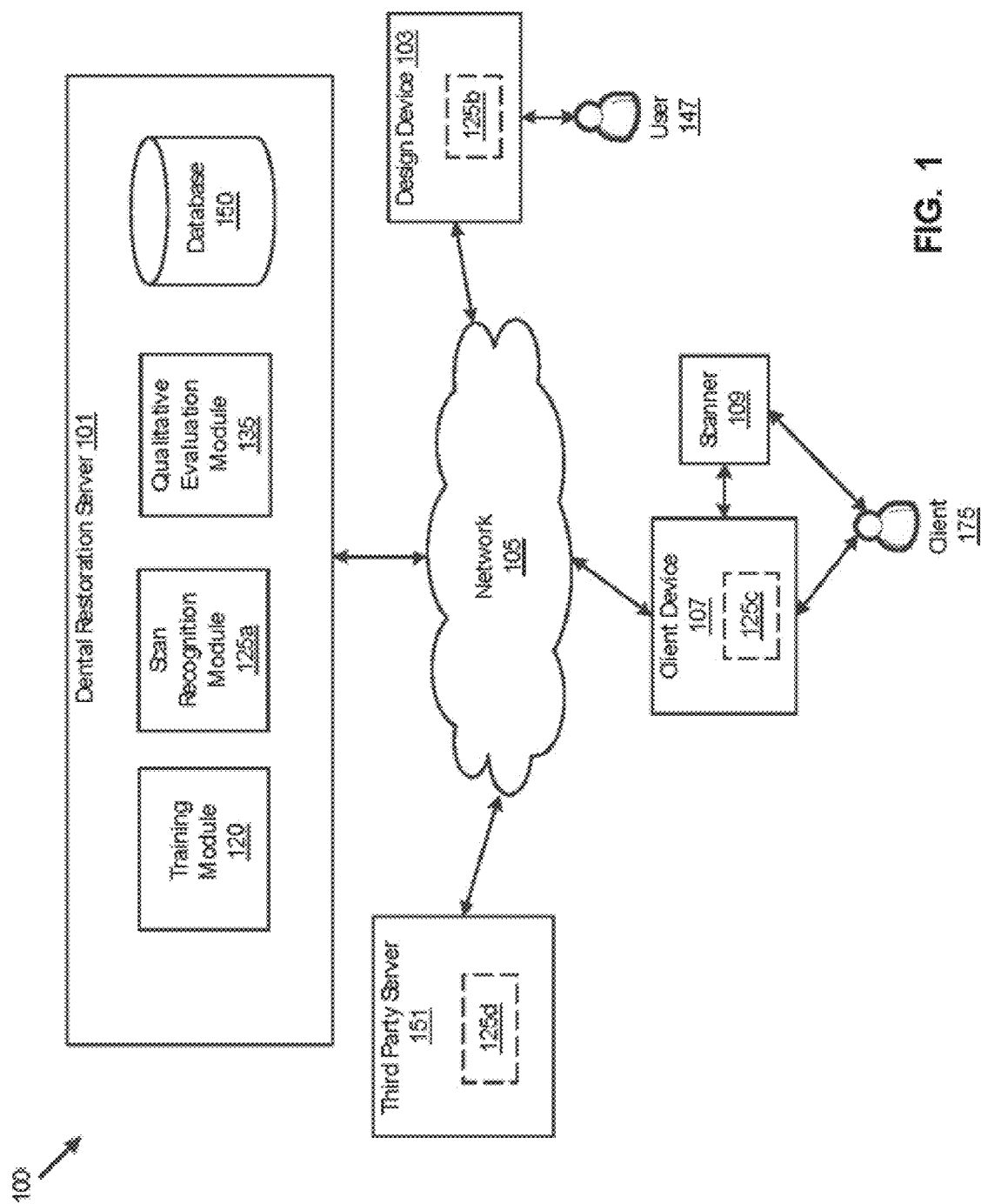
FIG. 1 is a high-level block diagram of a system for recognizing dental information from scan data of patients' dentitions and for designing dental restorations in accordance with some embodiments of the disclosure.

Systems for recognizing dental information or features from scan data of patients' dentitions and for designing dental restorations using deep neural networks are described below. In the following descriptions, for purposes of explanation, numerous specific details are set forth to provide a thorough understanding of the invention. However, it will be apparent to one skilled in the art that the invention can be practiced without these specific details. In other instances, structures and devices are shown in block diagram form in order to avoid obscuring the invention.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

Some portions of the following detailed description are presented in terms of algorithms and symbolic representations of operations on data bits within a computer memory. These algorithmic descriptions and representations are the methods used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared or otherwise manipulated. It has proven convenient at times, principally for reasons of common usage, to refer to these signals as bits, values, elements, symbols, characters, terms, numbers or the like.

It should be borne in mind, however, that all of these and similar terms are to be associated with the appropriate physical quantities and are merely convenient labels applied to these quantities. Unless specifically stated otherwise as apparent from the following disclosure, it is appreciated that throughout the disclosure terms such as "processing," "computing," "calculating," "determining," "displaying" or the like, refer to the action and processes of a computer system, or similar electronic computing device, that manipulates and transforms data represented as physical (electronic) quantities within the computer system's registers and memories into other data similarly represented as physical quantities within the computer system's memories or registers or other such information storage, transmission or display devices.

The present invention also relates to an apparatus for performing the operations herein. This apparatus may be specially constructed for the required purposes, or it may be a general-purpose computer selectively activated or reconfigured by a computer program stored in the computer. The invention may take the form of an entirely hardware embodiment, an entirely software embodiment or an embodiment including both hardware and software elements. In some embodiments, the invention is implemented in software comprising instructions or data stored on a computer-readable storage medium, which includes but is not limited to firmware, resident software, microcode or another method for storing instructions for execution by a processor.

Furthermore, the invention may take the form of a computer program product accessible from a computer-usable or computer-readable storage medium providing program code for use by, or in connection with, a computer or any instruction execution system. For the purposes of this description, a computer-usable or computer readable storage medium is any apparatus that can contain, store or transport the program for use by or in connection with the instruction execution system, apparatus or device. The computer-readable storage medium can be an electronic, magnetic, optical, electromagnetic, infrared, or semiconductor system (or apparatus or device) or a propagation medium. Examples of a tangible computer-readable storage medium include, but are not limited to, a semiconductor or solid state memory, magnetic tape, a removable computer diskette, a random access memory (RAM), a read-only memory (ROM), a rigid magnetic disk, an optical disk, an EPROM, an EEPROM, a magnetic card or an optical card, or any type of computer-readable storage medium suitable for storing electronic instructions, and each coupled to a computer system bus. Examples of optical disks include compact disk-read only memory (CD-ROM), compact disk-read/write (CD-R/W) and digital video disc (DVD).

A data processing system suitable for storing and/or executing program code includes at least one processor coupled directly or indirectly to memory elements through a system bus. The memory elements may include local memory employed during actual execution of the program code, bulk storage and cache memories providing temporary storage of at least some program code in order to reduce the number of times code must be retrieved from bulk storage during execution. In some embodiments, input/output (I/O) devices (such as keyboards, displays, pointing devices or other devices configured to receive data or to present data) are coupled to the system either directly or through intervening I/O controllers.

Network adapters may also be coupled to the data processing system to allow coupling to other data processing systems or remote printers or storage devices through intervening private or public networks. Modems, cable modem and Ethernet cards are just examples of the currently available types of network adapters.

Finally, the algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. It will be appreciated that a variety of programming languages may be used to implement the teachings of the invention as described herein.

The figures and the following description describe certain embodiments by way of illustration only. One skilled in the art will readily recognize from the following description that alternative embodiments of the structures and methods illustrated herein may be employed without departing from the principles described herein. Reference will now be made in detail to several embodiments, examples of which are illustrated in the accompanying figures. It is noted that wherever practicable similar or like reference numbers may be used in the figures to indicate similar or like functionality.

System Overview

Exemplary embodiments of methods and systems for recognizing dental information or features from scan data of patients' dentitions and for designing dental restorations using deep neural networks are described herein. The computer-implemented methods of designing dental restorations described herein use an electronic image of at least a portion of a patient's oral situation as a starting point for the design process. In some embodiments, the electronic image is obtained by a direct intraoral scan of the patient's teeth. This typically takes place, for example, in a dental office or clinic and be performed by a dentist or dental technician. In other embodiments, the electronic image is obtained indirectly by scanning an impression of the patient's teeth, by scanning a physical model of the patient's teeth, or by other methods known to those skilled in the art. This typically takes place, for example, in a dental laboratory and be performed by a laboratory technician. Accordingly, the methods described herein are suitable and applicable for use in chair side, dental laboratory, or other environments. Using the electronic image, a computer-implemented dental information or features recognition system is used to automatically identify useful dental structure and restoration information and detect features and margin lines of dentition, thus facilitating automatic dental restoration design and fabrication in following steps.

In some embodiments, a plurality of scans (e.g., 3-5 scans per quadrant) is performed in order to obtain a suitable image of the patient's anatomy. For example, an occlusal, lingual, and buccal scan may be taken of both the preparation and the opposing jaws. Then, a single scan with the jaws in occlusion may be taken from the buccal perspective to establish the proper occlusion relationship between the preparation jaw and the opposing jaw. Additionally, in some embodiments, interproximal scans are added to capture the contact areas of neighboring teeth. Once the scanning process is completed, a scanning system (not shown in FIGS) will assemble the plurality of scans into a digital model (also referred to as a "dental model" or "digital dental model" herein) of the preparation tooth and its surrounding and opposing teeth. The dental model can be used to design a restoration to be used on the preparation tooth. For example, a dental restoration design program may process and display the dental model in a user interface on a user device. A user (e.g., a design technician) operating on the user device can view the dental model and design or refine a restoration model based on the dental model.

In some embodiments, the present system may automatically recognize dental information and/or features from the dental model representing at least a portion of a patient's dentition and display the recognized dental information and/or features before the user starts doing manual design. For example, the present system may identify and label lower and upper jaws, prepared and opposing jaws, the number of tooth on which the preparation to be used, or the type of restoration to be designed. In other examples, the present system may also detect features, e.g., cusps, or margin line of the dentition for the user. Therefore, the user does not have to start the design from scratch and with the recognized dental information and features the user can accomplish the design more easily and fast. Further, in some situation, the automatically recognized dental information and features may function as check to guarantee the user performs the design appropriately.

In some embodiments, the present system may feed the recognized dental information and features to other auto-design programs for generating a restoration auto-proposal for users. For example, the auto-design programs can search a tooth library for the library tooth arch form that best matches the dentition in the dental model and position it automatically. By combining the recognized dental information and features into the proposed library tooth arch form, the present system further facilitates the users' design.

FIG. 1 shows a block diagram of a system 100 for recognizing dental information from scan data of patients' dentitions and for designing dental restorations in accordance with some embodiments of the present disclosure. System 100 includes a dental restoration server 101, a design device 103 operated by a user 147, a client device 107 and a scanner 109 operated by a client 175, and a third party server 151 connected by a network 105. Only one dental restoration server 101, one design device 103, one client device 107 and one third party server 151 are shown in FIG. 1 in order to simplify the description. Embodiments of system 100 can have multiple dental restoration servers 101, design devices 103, client devices 107 and third party servers 151 connected to the network 105. Likewise, the functions performed by the various entities of FIG. 1 may differ in different embodiments.

Network 105 enables communications among dental restoration server 101, design device 103, client device 107 and third party server 151. In some embodiments, network 105 uses standard communications technologies and/or protocols. For example, network 105 may be a conventional type of network, wired or wireless, and may have any number of configurations such as a star configuration, token ring configuration or other configurations known to one skilled in the related art. In another embodiment, the entities can use custom and/or dedicated data communications technologies instead of, or in addition to, the ones described above.

In some embodiments, network 105 comprises one or more of a local area network (LAN), a wide area network (WAN) (e.g., the Internet), and/or any other interconnected data path across which multiple devices communicate. In another embodiment, network 105 is a peer-to-peer network. Network 105 is coupled to or includes portions of a telecommunications network for sending data in a variety of different communication protocols. For example, network 105 is a 3G network or a 4G network. In yet another embodiment, the network 105 includes Bluetooth communication networks or a cellular communications network for sending and receiving data such as via short messaging service (SMS), multimedia messaging service (MMS), hypertext transfer protocol (HTTP), direct data connection, Wireless application protocol (WAP), email, etc. In yet another embodiment, all or some of the links in the network 105 are encrypted using conventional encryption technologies such as secure sockets layer (SSL), secure HTTP and/or virtual private networks (VPNs).

In some embodiments, network 105 is not a traditional network, but a cloud utilizing cloud computing techniques. Network/cloud 105 can incorporate any cloud servers. For example, dental restoration server 101 can be a cloud server incorporated in cloud 105. Third party server 151 can also be a cloud server included in cloud 105. By incorporating these servers, cloud 105 can provide cloud services to design device 103, and/or client device 107 by utilizing cloud computing techniques.

Dental restoration server 101 receives dental restoration requests from client device 107 operated by client 175 such as a human client. In some embodiments, the dental restoration requests include scan dental models generated by scanner 109. In other embodiments, client 107 may send physical model or impression of a patient's teeth along with the requests to dental restoration server 101 and the digital dental model can be created accordingly on the server side 101, e.g., by an administrator or technician operating on server 101. Dental restoration server 101 creates and manages dental restoration cases based upon the received requests from client 107. For example, dental restoration server 101 may assign the created cases to appropriate design device 103 or third party server 151 to design dental restoration according to the client's requests. When the cases have been completed, dental restoration server 101 may route the complete design back to client 107. In some embodiments, dental restoration server 101 may be incorporated in cloud 105 to provide dental restoration services described herein.

In some embodiments, dental restoration server 101 can train deep neural networks for automatic recognition of dental information from dental models and identifies dental information of dental models associated with dental restoration cases or requests using the previously trained deep neural networks. For example, the dental information may include lower and upper jaws, prepared and opposing jaws, tooth numbers, restoration types such as crown, inlay, bridge and implant, etc. Additional examples of dental information may include dental features (e.g., buccal and lingual cusps, occlusal surface, buccal and lingual arcs, etc.), margin lines, etc. In the illustrated embodiment, dental restoration server 101 includes a training module 120 and a scan recognition module 125a to perform the training of the deep neural networks and the automatic dental information recognition, respectively. The scan recognition module 125a, and 125b, 125c, 125d (which are described below with reference to corresponding devices or server) may be also individually or collectively referred to as the scan recognition module 125.

Dental restoration server 101 can have one or more deep neural networks, which can be part of training module 120 and/or qualitative evaluation module 135. Alternatively, the one or more deep neural networks can be an independent module residing within dental restoration server 101, remotely, or distributedly.

Dental restoration server 101 also includes a database 150 to store data related to the deep neural networks and the identified dental information associated with the dental models. Dental restoration server 101 may then feed the automatically identified dental information of the dental models to design device 103 or third party server 151 for facilitating the restoration design. Database 150 can also be remotely located from dental restoration server 101 or be distributedly located. In some embodiments, dental restoration server 101 may send the identified dental information of the dental models to client device 107 for the client's 175 review. Other embodiments of dental restoration server 101 may include different and/or additional components. Moreover, the functions may be distributed among the components in a different manner than described herein. Furthermore, system 100 may include a plurality of dental restoration servers 101 and/or other devices performing the work for a plurality of requesting clients 175.

Client device 107 can be an electronic device used by a human client 175 to perform functions such as receiving and/or reviewing scan dental models from scanner 109, submitting new dental restoration requests including dental models to dental restoration server 101 for design and/or fabrication, receiving and/or reviewing finished dental restoration model design from dental restoration server 101 through network 105, or receiving and/or checking identified dental information of the dental models. For example, client device 107 may be a smart phone, or a tablet, notebook, or desktop computer. Client device 107 includes and/or interfaces with a display device on which human client 175 may view the dental models, review the identified dental information of the dental models, or review complete dental restoration design. In addition, client device 107 provides a user interface (UI), such as physical and/or on-screen buttons, with which human client 175 may interact with client device 107 to perform functions such as submitting a new dental restoration request, receiving and reviewing identified dental information associated with dental models, receiving and reviewing a completed dental restoration design, etc. In some embodiments, client device 107 may include a scan recognition module 125c for automatic recognition of dental information associated with the dental models. Therefore, the device 107 can directly identify the dental information of the dental models for client 175 to review and check.

Scanner 109 may be any type of device for scanning a prepared tooth and its surroundings or a dental impression. Scanner 109 can generate a digital file of the scanned tooth and its surroundings or a teeth impression, and transmit the file to client device 107. For example, the digital file includes scan data and may represent a digital dental model. As described above, the dental model can be used by client 107 to create and send a dental restoration request to dental restoration server 101 for design and/or fabrication. In an alternative embodiment, client 175 can use the dental model to design the dental restoration on client device 107 by own.

Design device 103 may be interacted by user 147 to design dental restoration requested by client 107. In some embodiments, design device 103 may be a smart phone, or a tablet, notebook, or desktop computer. User 147 may be a human operator, dental technician or designer, etc. Design device 103 may receive dental restoration design assignment from dental restoration server 101 and perform the design accordingly. A design software (not shown in FIG. 1) used for digital design of the dental restoration can be installed in design device 103. The design software may provide library-based automatic dental restoration proposal for the user 147 to accelerate and simplify the design process. In some embodiments, design device 103 may include a scan recognition module 125b for automatic recognition of dental information associated with the dental models. With the dental information (e.g., lower and upper jaws, prepared and opposing jaws, tooth numbers, restoration types such as crown, inlay, bridge and implant, buccal and lingual cusps, occlusal surface, buccal and lingual arcs, margin lines, etc.)

being recognized, the design software can incorporate the dental information into the auto-proposal process to provide faster and better library-based restoration proposals.

The third party server 151 may be any one or more servers or devices providing dental restoration design to dental restoration server 101 through network 105. In some embodiments, third party server 151 may be required to conduct an agreement with dental restoration server 101. In some embodiments, third party server 151 includes computing devices equipped with the same or different design software (not shown in FIG. 1) from the software installed in design device 103. In the illustrated embodiment, third party server 151 may install a scan recognition module 125d for performing the dental information recognition function to facilitate the design. In some embodiments, third party server 151 may be included in the cloud 105 to provide dental restoration design and/or fabrication services.

In some embodiments, dental restoration server 101 trains deep neural networks to perform qualitative evaluations of restoration designs. For example, the system may perform qualitative evaluations of one or more aspects of a restoration design, such as the margin line fit, contact surfaces with adjacent teeth, occlusion with the teeth of the antagonist jaw, and contour of the restoration design. In the illustrated embodiment, dental restoration server 101 includes training module 120 and a qualitative evaluation module 135 to perform the training of the deep neural networks and the automatic qualitative evaluation, respectively.

Computing System Architecture

Figure 2:
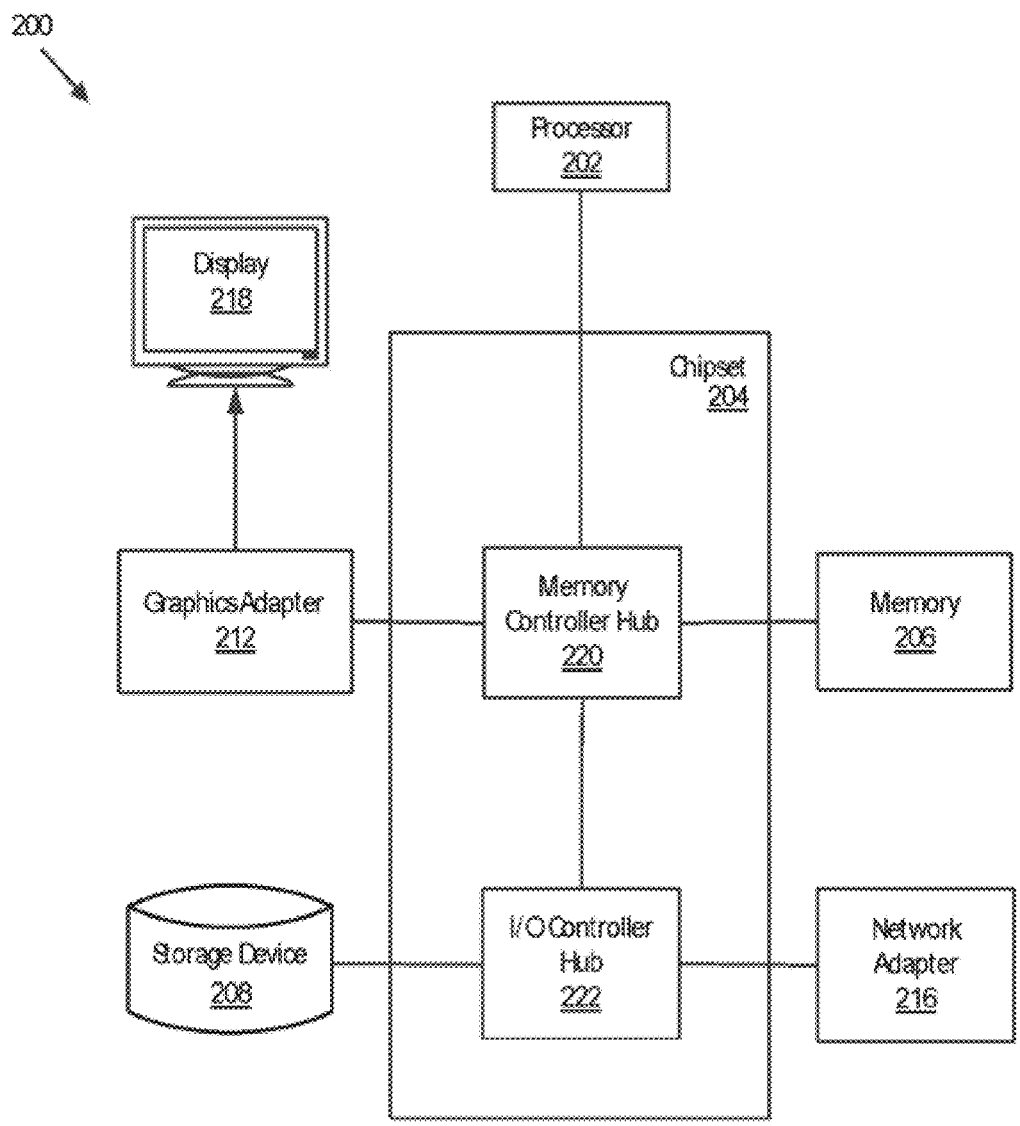
FIG. 2 is a high-level block diagram of a computing device in accordance with some embodiments of the present disclosure.

The entities shown in FIG. 1 are implemented using one or more computing devices. FIG. 2 is a high-level block diagram of a computing device 200 for acting as dental restoration server 101, design device 103, third party server 151, and/or client device 107, or a component of the above. Illustrated are at least one processor 202 coupled to a chipset 204. Also coupled to chipset 204 are a memory 206, a storage device 208, a graphics adapter 212, and a network adapter 216. A display 218 is coupled to the graphics adapter 212. In some embodiments, the functionality of the chipset 204 is provided by a memory controller hub 220 and an I/O controller hub 222. In another embodiment, memory 206 is coupled directly to processor 202 instead of chipset 204. Storage device 208 is any non-transitory computer-readable storage medium, such as a hard drive, compact disk read-only memory (CD-ROM), DVD, or a solid-state memory device. Memory 206 holds instructions and data used by processor 202. Graphics adapter 212 displays images and other information on the display 218. Network adapter 216 couples the computer system 200 to network 105.

As is known in the art, computing device 200 can have different and/or other components than those shown in FIG. 2. In addition, computing device 200 can lack certain illustrated components. Moreover, storage device 208 can be local and/or remote from the computing device 200 (such as embodied within a storage area network (SAN)).

As is known in the art, computing device 200 is adapted to execute computer program modules for providing functionality described herein. As used herein, the term "module" refers to computer program logic utilized to provide the specified functionality. Thus, a module can be implemented in hardware, firmware, and/or software. In some embodiments, program modules such as training module 120 and the scan recognition module 125 are stored on the storage device 208, loaded into memory 206, and executed by processor 202.

Prosthesis Generation Using Deep Neural Network

Figure 3:
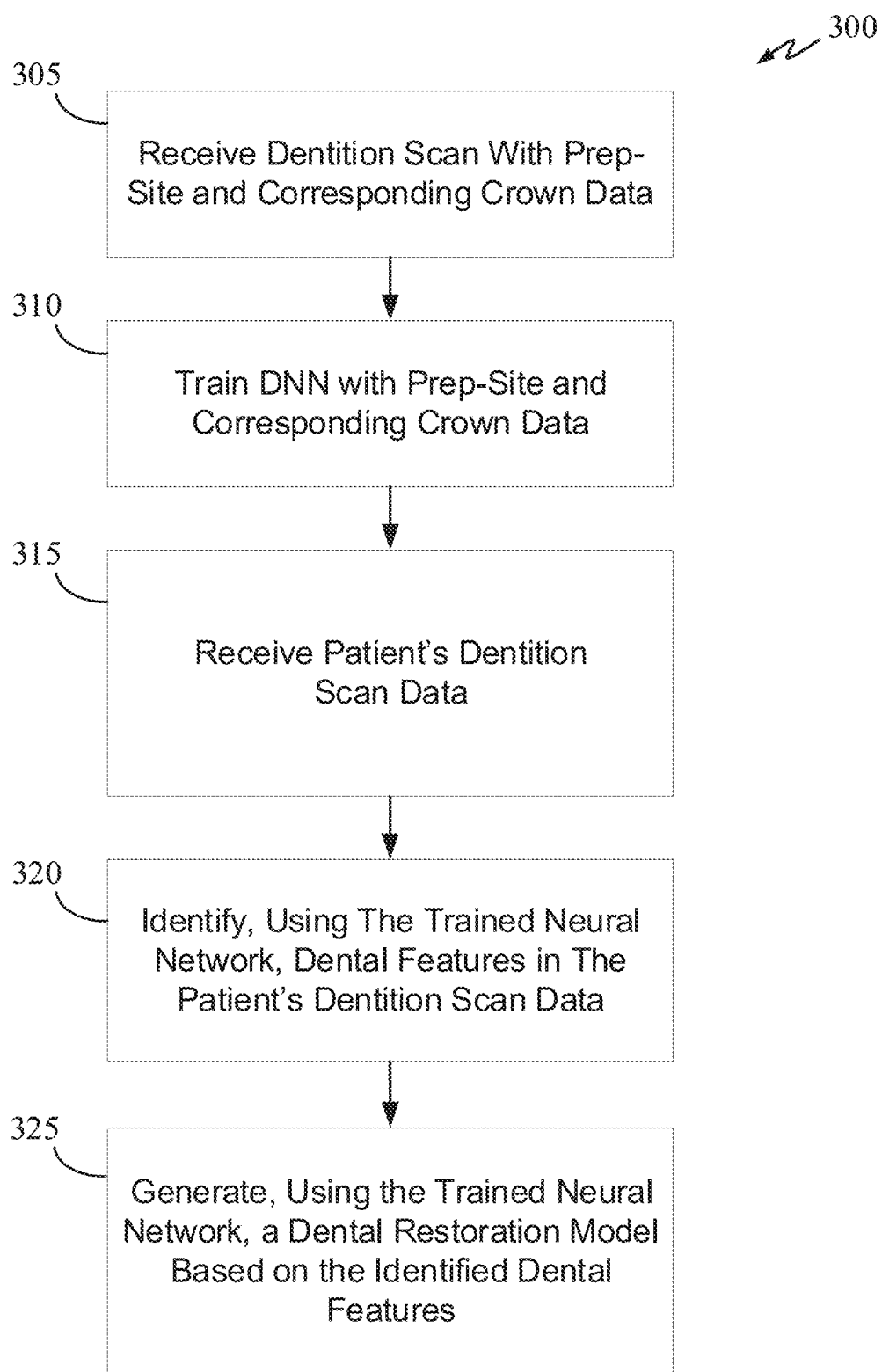
FIG. 3 is a flow chart of a process for generating a 3D dental prosthesis model using a deep neural network in accordance with some embodiments of the present disclosure.

FIG. 3 illustrates a dental prosthesis generation process 300 using a deep neural network (DNN). Process 300 starts at 305 where a dentition scan data set is received or ingested into a database such as database 150. The dentition scan data set can include one or more scan data sets of real patient's dentitions with dental preparation sites and technician-generated (non-DNN generated) dental prostheses created for those preparation sites. A dental preparation site (also referred to as a tooth preparation or a prepared tooth) is a tooth, a plurality of teeth, or an area on a tooth that has been prepared to receive a dental prosthesis (e.g., crown, bridge, inlay, etc.). A technician or a non-DNN generated dental prosthesis is a dental prosthesis mainly designed by a technician. Additionally, a technician-generated dental prosthesis can be designed based on a dental template library having a plurality of dental restoration templates. Each tooth in an adult mouth can have one or more dental restoration templates in the dental template library. More detail on the dental restoration library is provide below.

In some embodiments, the received dentition scan data set with dental preparation sites can include scan data of real patients' dentition having one or more dental preparation sites. A preparation site can be defined by a preparation margin. The received dentition scan data set can also include scan data of dental prostheses once they are installed on their corresponding dental preparation sites. This data set can be referred to as a dental prosthesis data set. In some embodiments, the dental prosthesis data set can include scan data of technician-generated prostheses before they are installed.

In some embodiments, each dentition scan data set received may optionally be preprocessed before using the data set as input of the deep neural network. Dentition scan data are typically 3D digital image or file representing one or more portions of a patient's dentition. The 3D digital image (3D scan data) of a patient's dentition can be acquired by intraorally scanning the patient's mouth. Alternatively, a scan of an impression or of a physical model of the patient's teeth can be made to generate the 3D scan data of a patient's dentition. In some embodiments, the 3D scan data can be transformed into a 2D data format using, for example, 2D depth maps and/or snapshots.

At 310, a deep neural network can be trained (by training module 120 for example) using a dentition scan data set having scan data of real dental preparation sites and their corresponding technician-generated dental prostheses—post installation and/or before installation. The above combination of data sets of real dental preparation sites and their corresponding technician-generated dental prostheses can be referred to herein as a technician-generated dentition scan data set. In some embodiments, the deep neural network can be trained using only technician-generated dentition scan data set. In other words, the training data only contain technician-generated dental prostheses, which were created based on one or more dental restoration library templates.

A dental template of the dental restoration library can be considered to be an optimum restoration model as it was designed with specific features for a specific tooth (e.g., tooth #3). In general, there are 32 teeth in a typical adult's mouth. Accordingly, the dental restoration library can have at least 32 templates. In some embodiments, each tooth template can have one or more specific features (e.g., sidewall size and shape, buccal and lingual cusp, occlusal surface, and buccal and lingual arc, etc.) that may be specific to one of the 32 teeth. For example, each tooth in the restoration library is designed to include features, landmarks, and directions that would best fit with neighboring teeth, surrounding gingiva, and the tooth location and position within the dental arch form. In this way, the deep neural network can be trained to recognize certain features (e.g., sidewall size and shape, cusps, grooves, pits, etc.) and their relationships (e.g., distance between cusps) that may be prominent for a certain tooth.

Training module 120 may train the deep neural network to recognize one or more dentition categories are present or identified in the training data set based on the output probability vector. For example, assume that the training data set contains a large number of depth maps representing patients' upper jaws and/or depth maps representing patients' lower jaws. Training module 120 can use the training data set to train the deep neural network to recognize each individual tooth in the dental arch form. Similarly, the deep neural network can be trained to map the depth maps of lower jaws to a probability vector including probabilities of the depth maps belonging to upper jaw and lower jaw, where the probability of the depth maps belonging to lower jaw is the highest in the vector, or substantially higher than the probability of the depth maps belonging to upper jaw.

In some embodiments, training module 120 may train a deep neural network, using dentition scan data set having one or more scan data sets of real dental preparation sites and corresponding technician-generated dental prostheses, to generate full 3D dental restoration model. In this way, the DNN generated 3D dental restoration model inherently incorporates one or more features of one or more tooth templates of the dental restoration library, which may be part of database 150.

Figure 4:
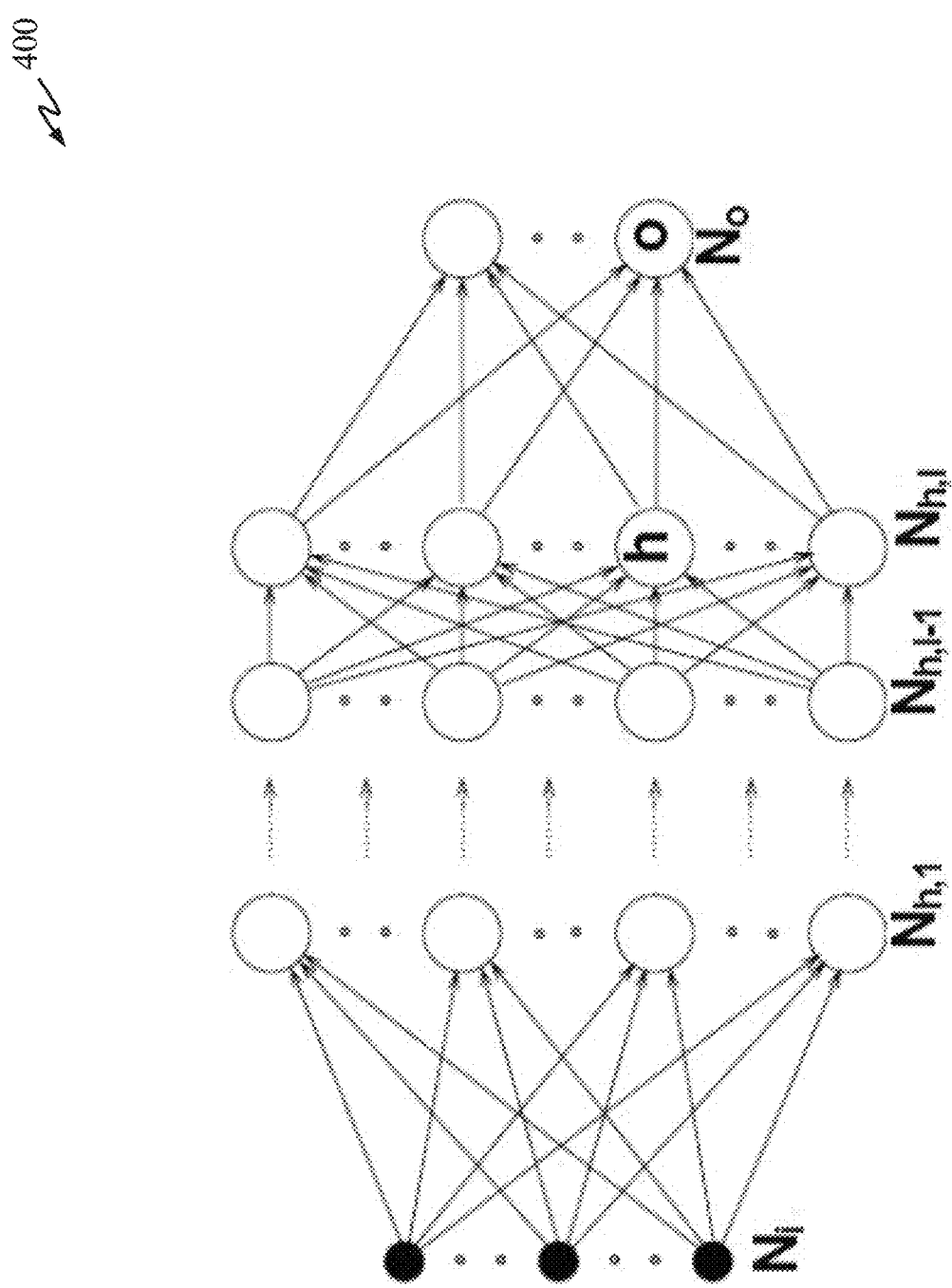
FIG. 4 is a high-level block diagram showing structure of a deep neural network in accordance with some embodiments of the present disclosure.

Referring now to FIG. 4, which is a high-level block diagram showing structure of a deep neural network (DNN) 400 according to some embodiments of the disclosure. DNN 400 includes multiple layers $N_i$, $N_{h,1}$, $N_{h,1-1}$, $N_{h,1}$, $N_O$, etc. The first layer $N_i$ is an input layer where one or more dentition scan data sets can be ingested. The last layer $N_O$ is an output layer. The deep neural networks used in the present disclosure may output probabilities and/or full 3D restoration model. For example, the output can be a probability vector that includes one or more probability values of each feature or aspect of the dental models belonging to certain categories. Additionally, the output can be a full 3D model of a dental restoration.

Each layer N can include a plurality of nodes that connect to each node in the next layer N+1. For example, each computational node in the layer $N_{h,\ 1-1}$ connects to each computational node in the layer $N_{h,1}$. The layers $N_{h,1}$, $N_{h,1-1}$, $N_{h,1}$, between the input layer $N_i$ and the output layer No are hidden layers. The nodes in the hidden layers, denoted as "h" in FIG. 4, can be hidden variables. In some embodiments, DNN 400 can include multiple hidden layers, e.g., 24, 30, 50, etc.

In some embodiments, DNN 400 may be a deep feedforward network. DNN 400 can also be a convolutional neural network, which is a network that uses convolution in place of the general matrix multiplication in at least one of the hidden layers of the deep neural network. DNN 400 may also be a generative neural network or a generative adversarial network. In some embodiments, training module 120 may use training data set with labels to supervise the learning process of the deep neural network. The labels are used to map a feature to a probability value of a probability vector. Alternatively, training module 120 may use unstructured and unlabeled training data sets to train, in an unsupervised manner, generative deep neural networks that do not necessarily require labeled training data sets.

Training module 120 can train a deep neural network to generate a 3D model of dental restoration using only the technician-designed dentition scan data set. In this way, the DNN generated 3D dental prosthesis will inherently include one or more features of dental prosthesis designed by a human technician using the library template. In some embodiments, training module 120 can train the deep neural network to output a probability vector that includes a probability of an occlusal surface of a technician-generated dental prosthesis representing the occlusal surface of a missing tooth at the preparation site or margin. Additionally, training module 120 can train a deep neural network to generate a complete 3D dental restoration model by mapping the occlusal surface having the highest probability and margin line data from the scanned dentition data to a preparation site. Additionally, training module 120 can train the deep neural network to generate the sidewall of the 3D dental restoration model by mapping sidewalls data of technician-generated dental prostheses to a probability vector that includes a probability of that one of the sidewalls matches with the occlusal surface and the margin line data from the preparation site.

Referring again to FIG. 3, to generate a new 3D model of a dental prosthesis for a new patient, the new patient's dentition scan data (e.g., scanned dental impression, physical model, or intraoral scan) received and ingested at 315. In some embodiments, the new patient's dentition scan data can be preprocessed to transform 3D image data into 2D image data, which can make the dentition scan data easier to ingest by certain neural network algorithms. At 320, using the previously trained deep neural network, one or more dental features in the new patient's dentition scan data are identified. The identified features can be a preparation site, the corresponding margin line, adjacent teeth and corresponding features, and surrounding gingiva for example.

At 325, using the trained deep neural network, a full 3D dental restoration model can be generated based on the identified features at 320. In some embodiments, the trained deep neural network can be tasked to generate the full 3D dental restoration model by: generating an occlusal portion of a dental prosthesis for the preparation site; obtaining the margin line data from the patient's dentition scan data; optionally optimizing the margin line; and generating a sidewall between the generated occlusal portion and the margin line. Generating an occlusal portion can include generating an occlusal surface having one or more of a mesiobuccal cusp, buccal grove, distobuccal cusp, distal cusp, distobuccal groove, distal pit, lingual groove, mesiolingual cusp, etc.

The trained deep neural network can obtain the margin line data from the patient's dentition scan data. In some embodiments, the trained deep neural network can optionally modify the contour of the obtained margin line by comparing and mapping it with thousands of other similar margin lines (e.g., margin lines of the same tooth preparation site) having similar adjacent teeth, surrounding gingiva, etc.

To generate the full 3D model, the trained deep neural network can generate a sidewall to fit between the generated occlusal surface and the margin line. This can be done by mapping thousands of sidewalls of technician-generated dental prostheses to the generated occlusal portion and the margin line. In some embodiments, a sidewall having the highest probability value (in the probability vector) can be selected as a base model in which the final sidewall between occlusal surface and the margin line will be generated.

Figure 5:
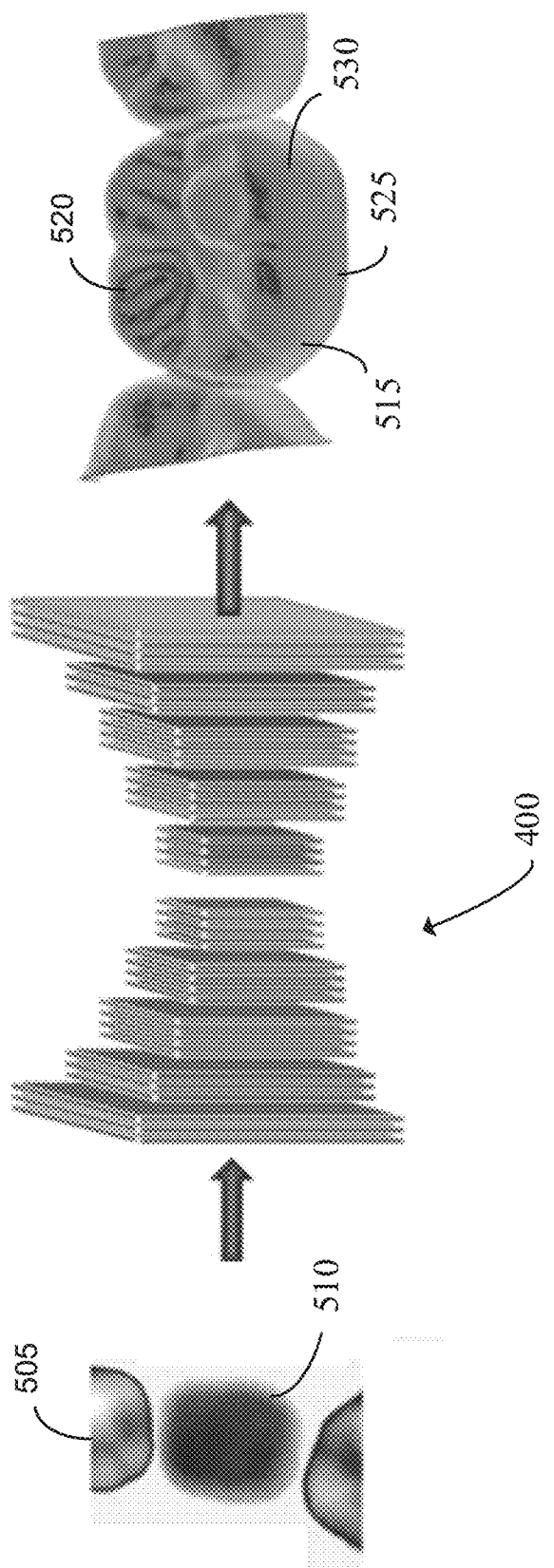
FIG. 5 is a graphic representation of input and output to a deep neural network in accordance with some embodiments of the present disclosure.

FIG. 5 illustrates example input and output of the trained deep neural network 400 (e.g., GAN) in accordance with some embodiments of the present invention. As shown, an input data set 505 can the new patient's dentition scan having a preparation site 510. Using the trained one or more deep neural network 400, dental restoration server 101 can generate a (DNN-generated) 3D model of a dental restoration 515. DNN-generated dental prosthesis 515 includes an occlusal portion 520, a margin line portion 525, and a sidewall portion 530. In some embodiments, the deep neural network can generate the sidewall for prosthesis 515 by analyzing thousands of technician-generated dental prostheses—which were generated based on one or more library templates—and mapping them to preparation site 510. Finally, the sidewall having the highest probability value can be selected as a model to generate sidewall 530.

Figure 6A:
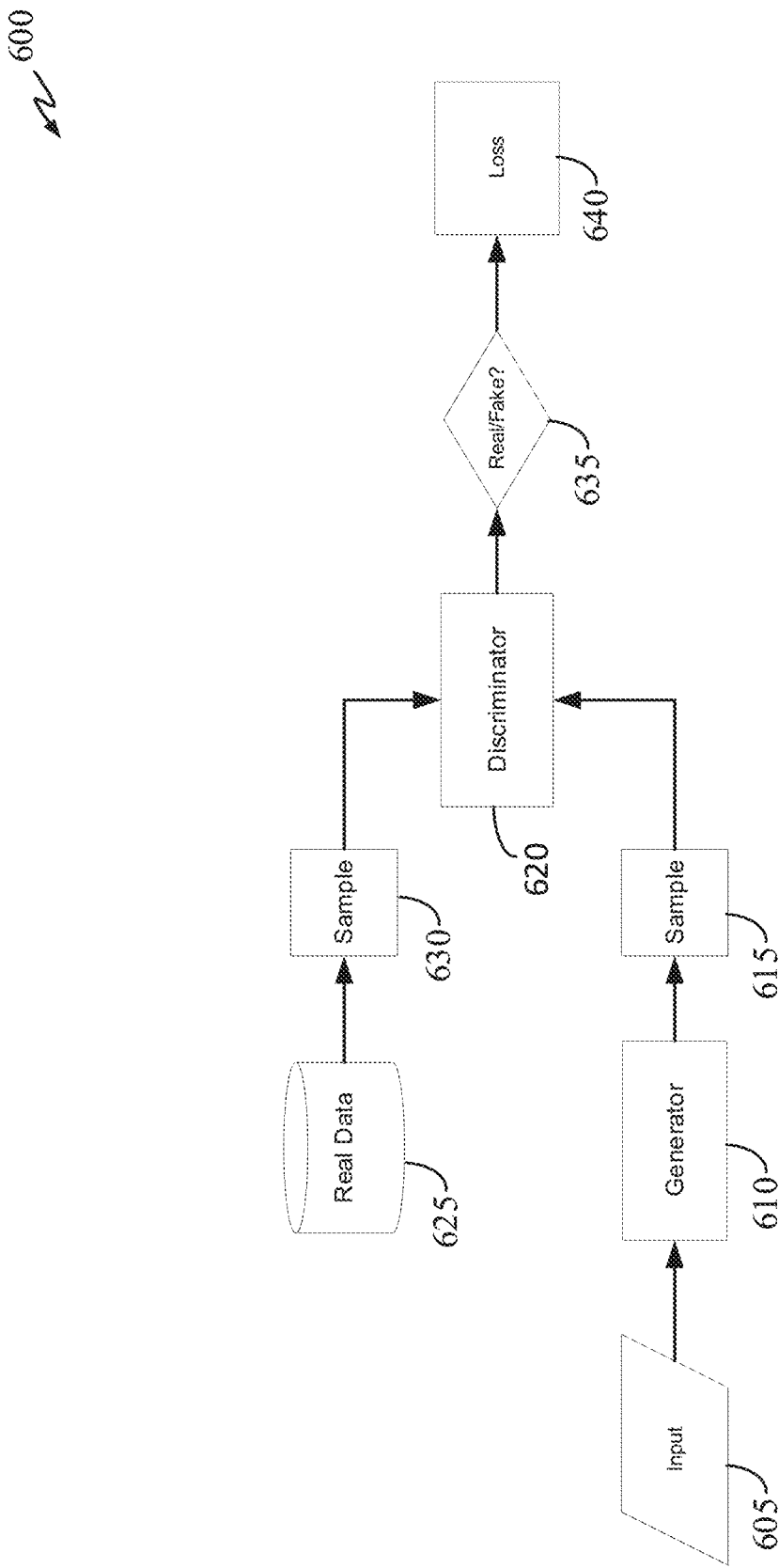
FIG. 6A-B are flow diagrams of methods for training a deep neural network to generate a 3D dental prosthesis in accordance with some embodiments of the present disclosure.

FIG. 6A is a high-level block diagram illustrating a structure of a generative adversarial network (GAN network) 600 that can be employed to identify and model dental anatomical features and restorations, in accordance with some embodiments of the present disclosure. On a high level, GAN network 600 uses two independent neural networks against each other to generate an output model that is substantially indistinguishable when compared with a real model. In other words, GAN network 600 employs a minimax optimization problem to obtain convergence between the two competing neural networks. GAN network 600 includes a generator neural network 610 and a discriminator neural network 620. In some embodiments, both neural network 610 and discriminator neural network 620 are deep neural networks structured to perform unstructured and unsupervised learning. In GAN network 600, both the generator network 610 and the discriminator network (discriminating deep neural network) 620 are trained simultaneously. Generator network 610 is trained to generate a sample 615 from the data input 605. Discriminator network 620 is trained to provide a probability that sample 615 belongs to a training data sample 630 (which comes from a real sample, real data 625) rather than one of the data sample of input 605. Generator network 610 is recursively trained to maximize the probability that discriminator network 620 fails to distinguish apart (at 635) a training data set and an output sample generated by generator 610.

At each iteration, discriminator network 620 can output a loss function 640, which is used to quantify whether the generated sample 615 is a real natural image or one that is generated by generator 610. Loss function 640 can be used to provide the feedback required for generator 610 to improve each succeeding sample produced in subsequent cycles. In some embodiments, in response to the loss function, generator 610 can change one or more of the weights and/or bias variables and generate another output In some embodiments, training module 120 can simultaneously train two adversarial networks, generator 610 and discriminator 620. Training module 120 can train generator 610 using one or more of a patient's dentition scan data sets to generate a sample model of one or more dental features and/or restorations. For example, the patient's dentition scan data can be 3D scan data of a lower jaw including a prepared tooth/site and its neighboring teeth. Simultaneously, training module 120 can train discriminator 620 to distinguish a generated a 3D model of a crown for the prepared tooth (generated by generator 610) against a sample of a crown from a real data set (a collection of multiple scan data set having crown images). In some embodiments, GAN networks are designed for unsupervised learning, thus input 605 and real data 625 (e.g., the dentition training data sets) can be unlabeled.

Figure 6B:
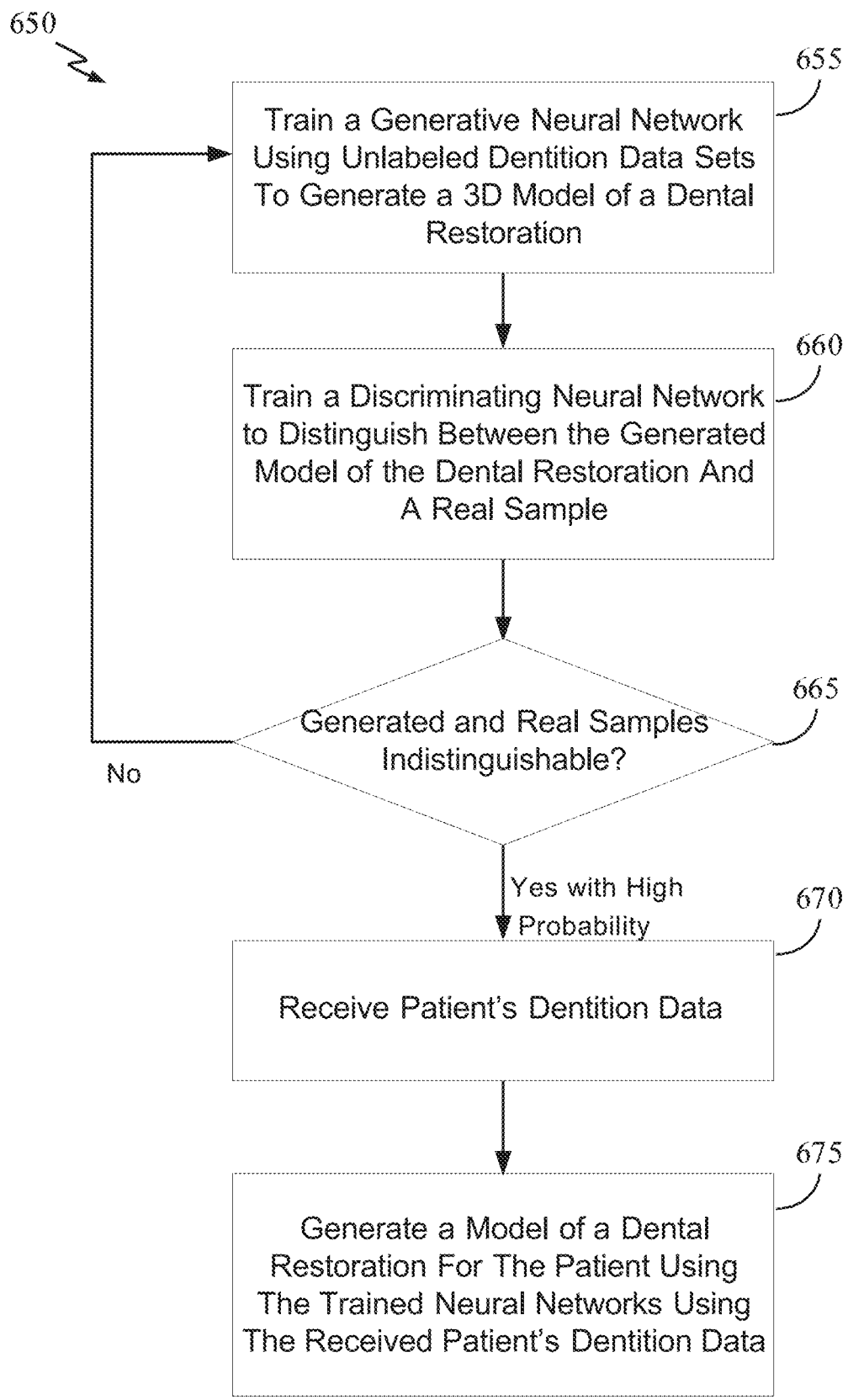

FIG. 6B is a flow chart of a method 650 for generating a 3D model of a dental restoration in accordance with some embodiments of the present disclosure. Method 650 can be performed by one or more modules of dental restoration server 101 such as training module 120. The instructions, processes, and algorithms of method 650 may be stored in memory 206 of computing device 200, and when executed by processor 202, they enable computing device 200 to perform the training of one or more deep neural networks for generating 3D dental prostheses. Some or all of the processes and procedures described in method 650 may be performed by one or more other entities or modules within restoration server 101 or within another remote computing device. In addition, one or more blocks (processes) of method 650 may be performed in parallel, in a different order, or even omitted.

At 655, training module 120 may train a generative deep neural network (e.g., GAN generator 610) using unlabeled dentition data sets to generate a 3D model of a dental prosthesis such as a crown. In one embodiment, labeled and categorized dentition data sets may be used, but not necessary. The generative deep neural network may reside in training module 120 or in a separate and independent neural network module, within or outside of dental restoration server 101.

At 660, and at substantially the same, training module 120 may also train a discriminating deep neural network (e.g., discriminator 620) to recognize that the dental restoration generated by the generative deep neural network is a model versus a digital model of a real dental restoration. In the recognition process, the discriminating deep neural network can generate a loss function based on comparison of a real dental restoration and the generated model of the dental restoration. The loss function provides a feedback mechanism for the generative deep neural network. Using information from the outputted loss function, the generative deep neural network may generate a better model that can better trick the discriminating neural network to think the generated model is a real model.

The generative deep neural network and the discriminating neural network can be considered to be adverse to each other. In other words, the goal of the generative deep neural network is to generate a model that cannot be distinguished by the discriminating deep neural network to be a model belonging a real sample distribution or a fake sample distribution (a generated model). At 665, if the generated model has a probability value indicating that it is most likely a fake, the training of both deep neural networks repeats and continues again at 655 and 660. This process continues and repeats until the discriminating deep neural network cannot distinguish between the generated model and a real model. In other words, the probability that the generated model is a fake is very low or that the probability that the generated model belong to a distribution of real samples is very high.

Once the deep neural networks are trained, method 600 is ready to generate a model of a dental restoration based on the patient's dentition data set, which is received at 670. At 675, a model of the patient's dentition data set is generated using the received patient's dentition data set.

Figure 7:
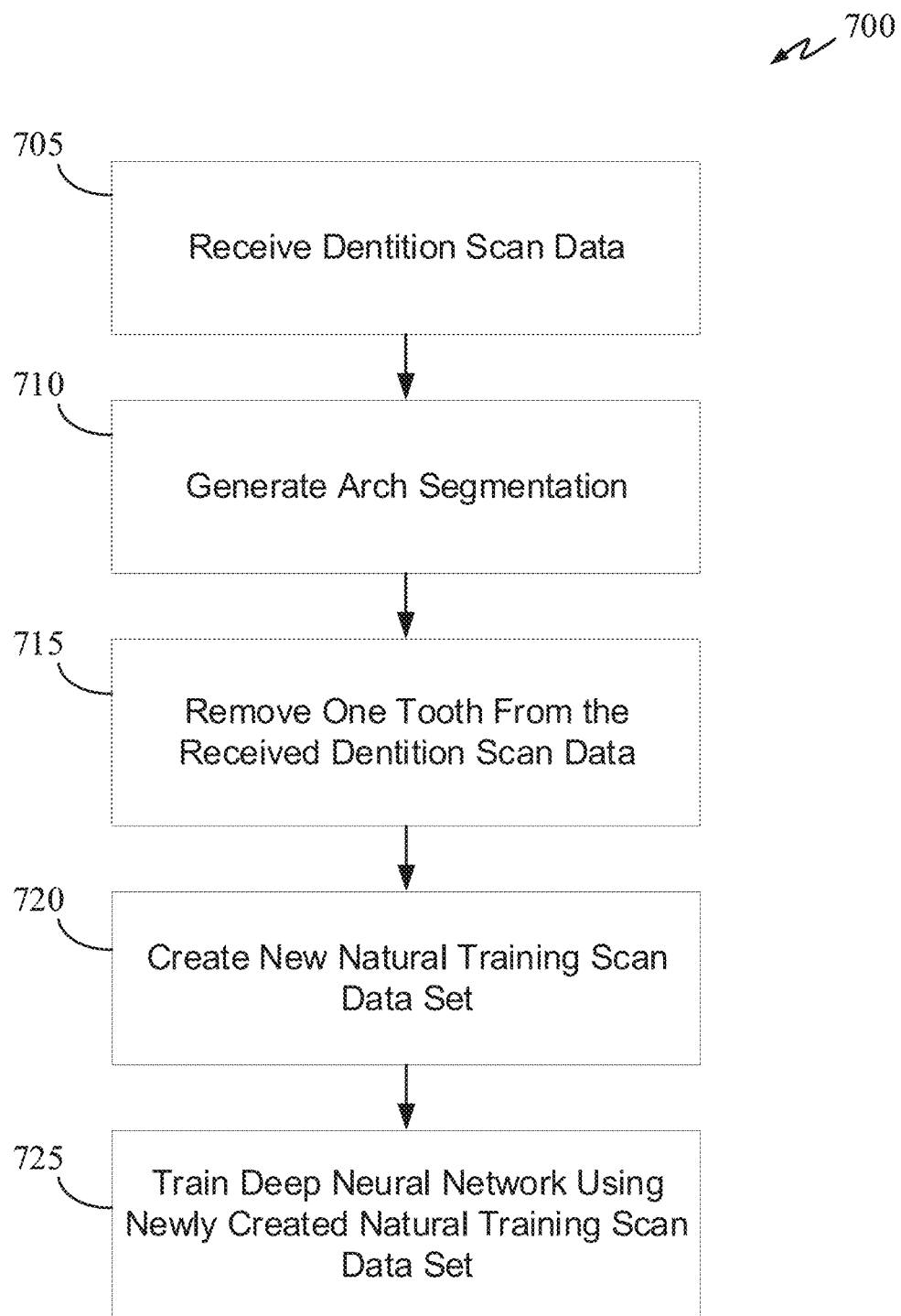
FIG. 7-8 are flow charts of methods for training deep neural networks to generate a 3D dental prosthesis in accordance with some embodiments of the present disclosure.

FIG. 7 illustrates a process 700 to generate a new natural dentition data set that can be used to train deep neural networks using arch segmentation in accordance with some embodiments of the present disclosure. Process 700 starts at 705 where one or more dentition scan data sets are received and ingested into database 150. In some embodiments, data ingestion of 3D format image can include transforming the 3D data into 2D data formats, which can be used to train a deep neural network to recognize various dental features, including individual tooth identification. At 710, a partial or full arch segmentation is performed on the received dentition scan data. The arch segmentation process can be useful for dentition identification and categorization. In other words, with the arch segmentation capability, dental restoration server 101 can use the trained deep neural network to identify the location and features of a preparation site and the tooth identifier (e.g., tooth #3) that a generated dental prosthesis should mimic. In another example, with arch segmentation capability, dental restoration server 101 can identify a scan of any individual tooth—without any data of neighboring teeth and/or surrounding gingiva.

In some embodiments, the arch segmentation process includes identifying and segmenting the dentition scan data into a plurality of individual tooth data components. For example, given a partial dentition scan having 4 teeth (number 1-4), the segmentation process can flag and/or separate out scan data into 4 separate data components. Each component represents scan data for each tooth. Thus, the segmentation process can modify the partial dentition scan data such that data for any of the four individual teeth can be selected, removed, and/or replaced. At 715, one of the data component for a tooth (e.g., tooth #2) can be deleted from the original scan dentition data of the 4-tooth arch form. In some embodiments, the data component for the deleted tooth can be replaced with a digitally created/fabricated preparation site or margin. Thus, the new dentition scan data for the new arch form (1 tooth extracted/deleted) includes 3 teeth and one preparation site.

In some embodiments, one of the useful applications for arch segmentation is to have the capability to generate an entirely new natural dentition data set (at 720) to train deep neural networks to generate naturally looking 3D model of dental prosthesis. A natural dentition scan data set as used herein has two main components. The first component is a data set that includes scanned dentition data of patients' natural teeth (ideally a full arch scan of top and bottom jaws). Data in the first component includes all of the patients' teeth in its natural and unmodified digital state. The second component of the natural dentition scan data is a missing-tooth data set with one or more teeth removed from the scanned data. In place of the missing-tooth, a DNN generated preparation site can be placed at the site of the missing-tooth. This process generates two sets of dentition data: a full and unmodified dentition scan data of patients' natural teeth; and a missing-tooth data set in which one or more teeth are digitally removed from the dentition scan data.

At 725, one or more deep neural networks are trained using the newly created natural training scan data set. Once a deep neural network is trained using the newly created natural training scan data set, it can be used to generate a natural 3D dental prosthesis. It should be noted that one of the main differences between dental prosthesis generation processes 300 and 700 is that the DNN-generated 3D model generated from process 300 is based on technician-generated dental prosthesis (which in turn is based off a dental restoration template) and the DNN-generated 3D model generated from process 700 is based of patients' natural dentition features. The former DNN-generated 3D model can be considered to be more technically perfect than its natural based counterpart since it is created based on a carefully engineered library template.

Customized Training and Model Generation

Figure 8:
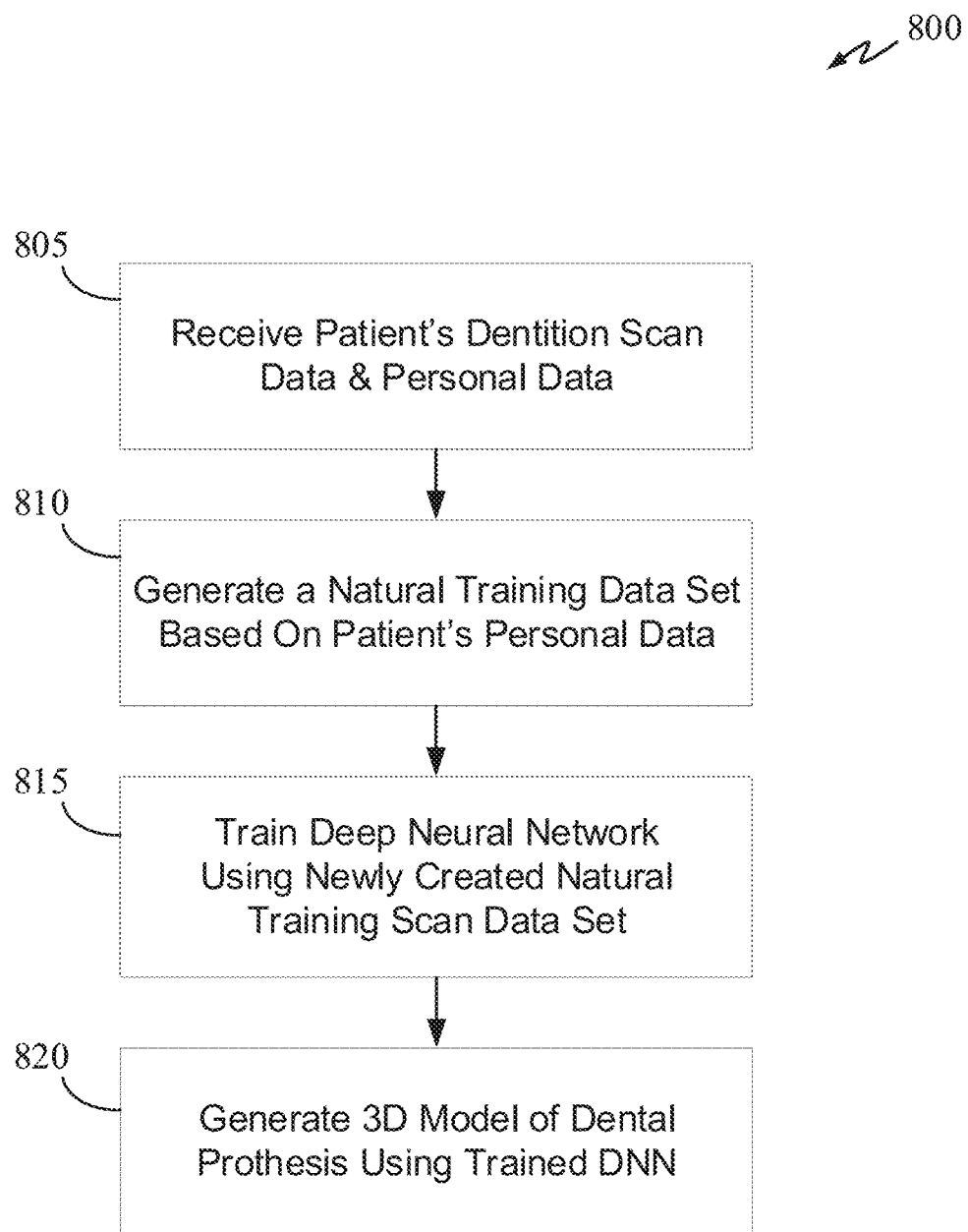

FIG. 8 illustrates a process 800 for customizing the training data set in order to generate a customized DNN-generated dental prosthesis in accordance with some embodiments of the present disclosure. At 805, a patient's dentition scan data and personal data are received. Personal data may include the patient's age, gender, ethnicity, diet, lifestyle, and other information that can provide insight on the patient's dentition or can create groups or classes of patient. At 810, a natural training data set is generated based on the patient's personal data. A customized training data set from people with similar age, diet, and lifestyle can lead to a more desirable DNN-generated 3D dental prosthesis. For example, a septuagenarian patient may want a DNN-generated crown that looks similar to other septuagenarians' natural tooth so that the DNN-generate crown does not look artificial once installed. In another example, a patient from Southeastern United States and who smokes tobacco products may want a DNN-generated crown that looks similar to other people in Southeastern United States who also smoke tobacco products. Accordingly, each dentition data set can be categorized and classified by one or more personal data. In some embodiments, the dentition data set classification can be done by dental restoration server 101 or manually.

A natural dentition training data set is created by selecting dentition scan data that match with the patient's personal data such as age, gender, diet, lifestyle, etc. As previously mentioned, a natural training data set has two main components. The first component is a collection of scanned dentition data of patients' natural teeth (ideally a full arch scan of top and bottom jaws). Using the above example, only dentition scan data of people in Southeastern United States will be used. And if available, only dentition scan data of tobacco users will be used. The second component of the natural dentition scan data is a missing-tooth data set with one or more teeth removed from the scanned data. In place of the missing-tooth, a DNN generated preparation site can be placed at the site of the missing-tooth. Again, this process generates two sets of dentition data for the natural training data set: a full and unmodified dentition scan data of patients' natural teeth; and a missing-tooth data set in which one or more teeth are digitally removed from the dentition scan data, which can be referred to herein as a natural dental prosthesis data set.

At 815, the natural training data set is used to train a deep neural network to generate a full 3D model of a dental prosthesis. At 820, the trained deep neural network can generate the full 3D model of the dental prosthesis based on received patient's dentition scan data. Although a 3D dental prosthesis generated by process 300 is very good from a dentition perspective, the 3D dental prosthesis generated by process 800 using customized training data set can be more desirable to the patient and may look more natural because of inherent imperfections (e.g., less distinctive cusps and grooves and more blended features).

Figure 9B:
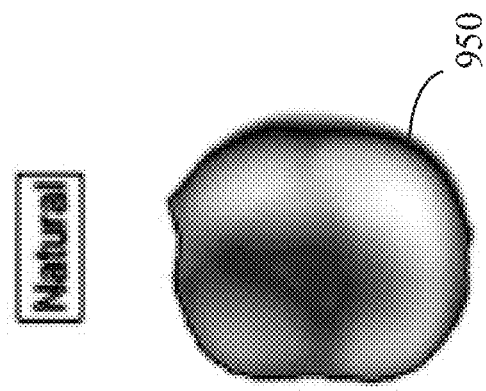
FIGS. 9A-9B illustrate examples crowns generated using deep neural networks in accordance with some embodiments of the present disclosure.
Figure 9A:
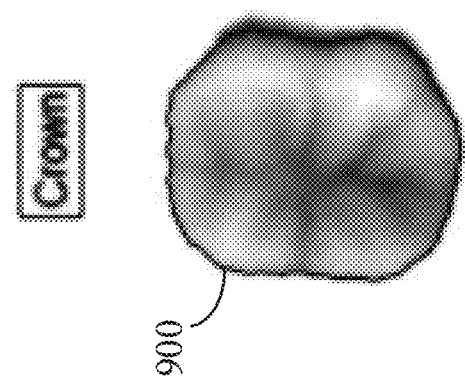

FIG. 9A illustrates an example DNN-generated crown 900 using process 300, which uses a DNN that has been trained using technician-generated crowns. As previously mentioned, technician-generated crowns are more "perfect" looking because they are based on a carefully engineered dental template of dental restoration library. As shown, crown 900 has distinctive grooves and cusp. FIG. 9B illustrates an example DNN-generated crown 950 is generated using process 700 or 800, which uses a DNN that has been trained using a natural dentition training data set. As shown, crown 950 has blended features (i.e., cusps and grooves are not distinctive and blended). Although crown 950 may appear to be less perfect than crown 900, it may still be desirable over crown 900 because it may fit in better with the surrounding teeth. For example, if substantially all of the septuagenarian's teeth are worn, installing crown 900 would immediately stand out. Accordingly, in this case, crown 950 may be more desirable for the septuagenarian patient.

FIGS. 10A-B illustrate an exemplary user interface 1000 to generate a blended crown by transferring/combining one or more features of crown 950 into crown 900 in accordance with some embodiments of the present disclosure. User interface 1000 includes a natural crown window 1005, an engineered-crown window 1010, a blended-crown window 1015, a boundary/contour slide bar 1020, and an anatomy slide bar 1025. As shown, natural crown window displays DNN-generated crown using process 700 or 800. Engineered-crown (e.g., crowns generated using technician-generated crown data) window 1010 displays DNN-generated crown using process 300, and blended-crown window displays a crown having blended features from both natural and engineered crown.

To add more contour and/or more features to the natural crown in window 1005, the user can slide the bar on slide bar 1020 and/or slide bar 1025 and the trained DNN will automatically transfer one or more features of the contour and anatomy of the engineered-crown in window 1010 to the natural crown in window 1005. The result of the feature transfer function is the blended crown 1025 or 1030. As shown in FIG. 10B, a maximum amount of anatomy is selected using the slide bar. Accordingly, blended crown 1030 has very similar or identical features as engineered crown.

The above description is included to illustrate the operation of the preferred embodiments and is not meant to limit the scope of the invention. The scope of the invention is to be limited only by the following claims. From the above discussion, many variations will be apparent to one skilled in the relevant art that would yet be encompassed by the spirit and scope of the invention.

The foregoing description of the embodiments of the present invention has been presented for the purposes of illustration and description. It is not intended to be exhaustive or to limit the present invention to the precise form disclosed. Many modifications and variations are possible in light of the above teaching. It is intended that the scope of the present invention be limited not by this detailed description, but rather by the claims of this application. As will be understood by those familiar with the art, the present invention may be embodied in other specific forms without departing from the spirit or essential characteristics thereof. Likewise, the particular naming and division of the modules, routines, features, attributes, methodologies and other aspects are not mandatory or significant, and the mechanisms that implement the present invention or its features may have different names, divisions and/or formats.

Furthermore, as will be apparent to one of ordinary skill in the relevant art, the modules, routines, features, attributes, methodologies and other aspects of the present invention can be implemented as software, hardware, firmware or any combination of the three. Also, wherever a component, an example of which is a module, of the present invention is implemented as software, the component can be implemented as a standalone program, as part of a larger program, as a plurality of separate programs, as a statically or dynamically linked library, as a kernel loadable module, as a device driver, and/or in every and any other way known now or in the future to those of ordinary skill in the art of computer programming.

Additionally, the present invention is in no way limited to implementation in any specific programming language, or for any specific operating system or environment. Accordingly, the disclosure of the present invention is intended to be illustrative, but not limiting, of the scope of the present invention, which is set forth in the following claims.

What is claimed is:

1. A computer-implemented method for generating dental restoration associated with dental model of dentition, the method comprising:
    training, by one or more computing devices, a deep neural network to generate a first 3D dental prosthesis model using a training data set;
    receiving, by the one or more computing devices, a patient scan data representing at least a portion of a patient's dentition; and
    generating, using the trained deep neural network, the first 3D dental prosthesis model based on the received patient scan data
    wherein the deep neural network comprises a generative adversarial network (GAN).

2. The method of claim 1, wherein the training data set comprises a dentition scan data set with preparation site data and a dental prosthesis data set, wherein the dental prosthesis data set comprises scanned prosthesis data associated with each preparation site in the dentition scan data set.

3. The method of claim 2, wherein the dental prosthesis data set comprises scanned data of real crowns created based on a library tooth template.

4. The method of claim 3, wherein the library comprises 32 tooth templates.

5. The method of claim 4, wherein the real crowns are created by technicians using the 32 tooth templates.

6. The method of claim 2, wherein the dentition scan data set with preparation site data comprises scanned data of real preparation sites from patients' scanned dentitions.

7. The method of claim 2, further comprising:
    training a second deep neural network to generate a second 3D dental prosthesis model using a natural dentition scan data set with digitally fabricated preparation site data and a natural dental prosthesis data set, wherein the natural dental prosthesis data set comprises segmented tooth associated with each digitally fabricated preparation site in the dentition scan data set; and
    generating, using the second deep neural network, the second 3D dental prosthesis model based on the received patient scan data.

8. The method of claim 7, further comprising blending together features of the first and second 3D dental prosthesis models to generate a blended 3D dental prosthesis model.

9. The method of claim 7, further comprising:
    receiving a patient's profile information; and
    selecting one or more dentition scan data sets that match with the patient's profile information, wherein the natural dentition scan data only include matched dentition scan data sets.

10. The method of claim 1, wherein the dental prosthesis comprises a crown, an inlay, a bridge or an implant.

11. The method of claim 1, wherein the training data set comprises a natural dentition scan data set with digitally fabricated preparation site data and a natural dental prosthesis data set, wherein the dental prosthesis data set comprises segmented tooth data associated with each digitally fabricated preparation site in the dentition scan data set.

12. The method of claim 11, wherein the segmented tooth data are generated by segmenting tooth data from the natural dentition scan data set.

13. A computer program product comprising a computer-readable storage medium having computer program logic recorded thereon for enabling a processor-based system to generate a 3D dental prosthesis model, the computer program product comprising:
- a first program logic module for enabling the processor-based system to train a deep neural network to generate a first 3D dental prosthesis model using a training data set;
- a second program logic module for enabling the processor-based system to receive a patient scan data representing at least a portion of a patient's dentition; and
- a third program logic module for enabling the processor-based system to generate the first 3D dental prosthesis model based on the received patient scan data
- wherein the deep neural network comprises a generative adversarial network (GAN).

14. The computer program product of claim 13, wherein the training data set comprises a dentition scan data set with preparation site data and a dental prosthesis data set, wherein the dental prosthesis data set comprises scanned prosthesis data associated with each preparation site in the dentition scan data set.

15. The computer program product of claim 14, wherein the dental prosthesis data set comprises scanned data of real crowns created based on a library tooth template.

16. The computer program product of claim 15, wherein the library comprises 32 tooth templates.

17. The computer program product of claim 16, wherein the real crowns are created by technicians using the 32 tooth templates.

18. The computer program product of claim 14, wherein the dentition scan data set with preparation site data comprises scanned data of real preparation sites from patients' scanned dentitions.

19. The computer program product of claim 14, further comprises:
- a fourth program logic module for enabling the processor-based system to train a second deep neural network to generate a second 3D dental prosthesis model using a natural dentition scan data set with digitally fabricated preparation site data and a natural dental prosthesis data set, wherein the natural dental prosthesis data set comprises segmented tooth associated with each digitally fabricated preparation site in the dentition scan data set; and
- a fifth program logic module for enabling the processor-based system to generate, using the second deep neural network, the second 3D dental prosthesis model based on the received patient scan data.

20. The computer program product of claim 19, further comprises a sixth program logic module for enabling the processor-based system to blend together features of the first and second 3D dental prosthesis models to generated a blended 3D dental prosthesis model.

21. The computer program product of claim 13, wherein the training data set comprises a natural dentition scan data set with digitally fabricated preparation site data and a natural dental prosthesis data set, wherein the dental prosthesis data set comprises segmented tooth data associated with each digitally fabricated preparation site in the dentition scan data set.

22. The computer program product of claim 21, wherein the segmented tooth data are generated by segmenting tooth data from the natural dentition scan data set.

\* \* \* \* \*